(12) United States Patent
Kobayashi et al.

(10) Patent No.: US 12,036,056 B2
(45) Date of Patent: Jul. 16, 2024

(54) X-RAY TUBE HOLDING APPARATUS AND X-RAY IMAGING SYSTEM

(71) Applicant: CANON MEDICAL SYSTEMS CORPORATION, Otawara (JP)

(72) Inventors: Yoshimasa Kobayashi, Nasushiobara (JP); Haruki Iwai, Otawara (JP); Toshikatsu Oohashi, Otawara (JP); Masato Akimoto, Sakura (JP); Takehito Tomaru, Otawara (JP); Takehiro Fukuzaki, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 22 days.

(21) Appl. No.: 17/412,681

(22) Filed: Aug. 26, 2021

(65) Prior Publication Data
US 2022/0061788 A1 Mar. 3, 2022

(30) Foreign Application Priority Data

Sep. 1, 2020 (JP) ................................. 2020-147029

(51) Int. Cl.
*A61B 6/00* (2024.01)
*A61B 6/02* (2006.01)
(Continued)

(52) U.S. Cl.
CPC ............ *A61B 6/4405* (2013.01); *A61B 6/548* (2013.01); *B64C 39/024* (2013.01); *B64F 1/36* (2013.01);
(Continued)

(58) Field of Classification Search
CPC ....... A61B 6/4405; A61B 6/548; A61B 6/025; A61B 6/588; A61B 6/4452; A61B 6/44;
(Continued)

(56) References Cited

U.S. PATENT DOCUMENTS

2013/0233964 A1* 9/2013 Woodworth ............ B64C 27/20
244/175
2019/0047699 A1* 2/2019 Bonden ............... H01M 10/613
(Continued)

FOREIGN PATENT DOCUMENTS

| CN | 111132618 A | 5/2020 |
|---|---|---|
| JP | 2019-523687 A | 8/2019 |
| WO | WO 2019/063434 A1 | 4/2019 |

OTHER PUBLICATIONS

Office Action mailed Jan. 23, 2024 in Japanese Application No. 2020-147029 filed Sep. 1, 2020.
(Continued)

*Primary Examiner* — Rachid Bendidi
*Assistant Examiner* — Dana F Artimez
(74) *Attorney, Agent, or Firm* — Oblon, McClelland, Maier & Neustadt, L.L.P.

(57) ABSTRACT

The X-ray imaging system according to the present embodiment includes an X-ray tube, a holding assembly, a flying object, an X-ray detector, and processing circuitry, The X-ray tube is configured to emit X-rays. The holding assembly is configured to hold the X-ray tube. The flying object is equipped with the holding assembly. The X-ray detector is configured to detect the X-rays emitted by the X-ray tube. The processing circuitry is configured to control a flight of the flying object, and to control the flight of the flying object such that the X-ray tube is arranged on a predetermined position with respect to the X-ray detector.

19 Claims, 11 Drawing Sheets

(51) Int. Cl.
  *B64C 39/02* (2023.01)
  *B64F 1/36* (2017.01)
  *B64U 10/13* (2023.01)
  *G05D 1/00* (2006.01)
  *H05G 1/10* (2006.01)
  *H05G 1/30* (2006.01)
  *B64U 101/00* (2023.01)

(52) U.S. Cl.
  CPC .......... *G05D 1/0094* (2013.01); *G05D 1/106* (2019.05); *H05G 1/10* (2013.01); *H05G 1/30* (2013.01); *A61B 6/025* (2013.01); *B64U 10/13* (2023.01); *B64U 2101/00* (2023.01); *B64U 2201/104* (2023.01)

(58) Field of Classification Search
  CPC ....... A61B 6/4208; B64C 39/024; B64F 1/36; G05D 1/0094; G05D 1/106; H05G 1/10; H05G 1/30; B64U 10/13; B64U 2101/00; B64U 2201/104; B64U 2101/30
  See application file for complete search history.

(56) References Cited

U.S. PATENT DOCUMENTS

| | | | |
|---|---|---|---|
| 2019/0126057 | A1 | 5/2019 | Feldreich |
| 2019/0145912 | A1* | 5/2019 | Sijbers .................. G01N 23/04 378/62 |
| 2020/0187891 | A1* | 6/2020 | Gotoh ..................... A61B 6/52 |
| 2020/0239138 | A1* | 7/2020 | Raptopoulos ......... B64C 39/024 |
| 2020/0281549 | A1* | 9/2020 | Steadman Booker . A61B 6/587 |
| 2021/0047053 | A1* | 2/2021 | Sugimoto ................ B64F 1/22 |
| 2022/0240876 | A1* | 8/2022 | Gudde .................... G21K 1/04 |
| 2022/0334037 | A1* | 10/2022 | Jones ...................... G01N 9/24 |

OTHER PUBLICATIONS

Office Action mailed Mar. 22, 2024 in Chinese Application No. 202110992408.1 filed Aug. 27, 2021.

* cited by examiner

X-RAY TUBE HOLDING APPARATUS AND X-RAY IMAGING SYSTEM

CROSS-REFERENCE TO RELATED APPLICATION

This application is based upon and claims the benefit of priority from Japanese Patent Application No. 2020-147029, filed on Sep. 1, 2020, the entire contents of which are incorporated herein by reference.

FIELD

An embodiment disclosed in the present specification and drawings relates to an X-ray tube holding apparatus and an X-ray imaging system.

BACKGROUND

Conventionally, an X-ray imaging system has been widely used in an industrial field such as a non-destructive inspection and a medical field such as a medical examination. The X-ray imaging system emits radiation (typically, X-ray) to an examination region (e.g., chest) of a subject and detects the intensity distribution of X-rays that have passed through the examination region as transparent data, thereby generating X-ray image data based on the transparent data. The X-ray imaging system is able to perform X-ray emission to acquire transparent data, and generate X-ray image data by performing image processing or the like on the transparent data.

In the X-ray imaging system, a distance between focus detectors (SID: Source to image receptor distance) is particularly important in order to acquire X-ray image data useful for diagnosis in X-ray imaging of the chest and cervical spine. However, in the conventional X-ray imaging system, it may sometimes be difficult to acquire the X-ray image data related to the desired SID due to restrictions on the arrangement of the X-ray tube, the X-ray detector, and the like.

DETAILED DESCRIPTION

An X-ray tube holding apparatus and an X-ray imaging system according to a present embodiment will be described with reference to the accompanying drawings.

The X-ray imaging system according to the present embodiment includes an X-ray tube, a holding assembly, a flying object, an X-ray detector, and processing circuitry. The X-ray tube is configured to emit X-rays. The holding assembly is configured to hold the X-ray tube. The flying object is equipped with the holding assembly. The X-ray detector is configured to detect the X-rays emitted by the X-ray tube. The processing circuitry is configured to control a flight of the flying object, and to control the flight of the flying object such that the X-ray tube is arranged on a predetermined position with respect to the X-ray detector.

Figure 1:
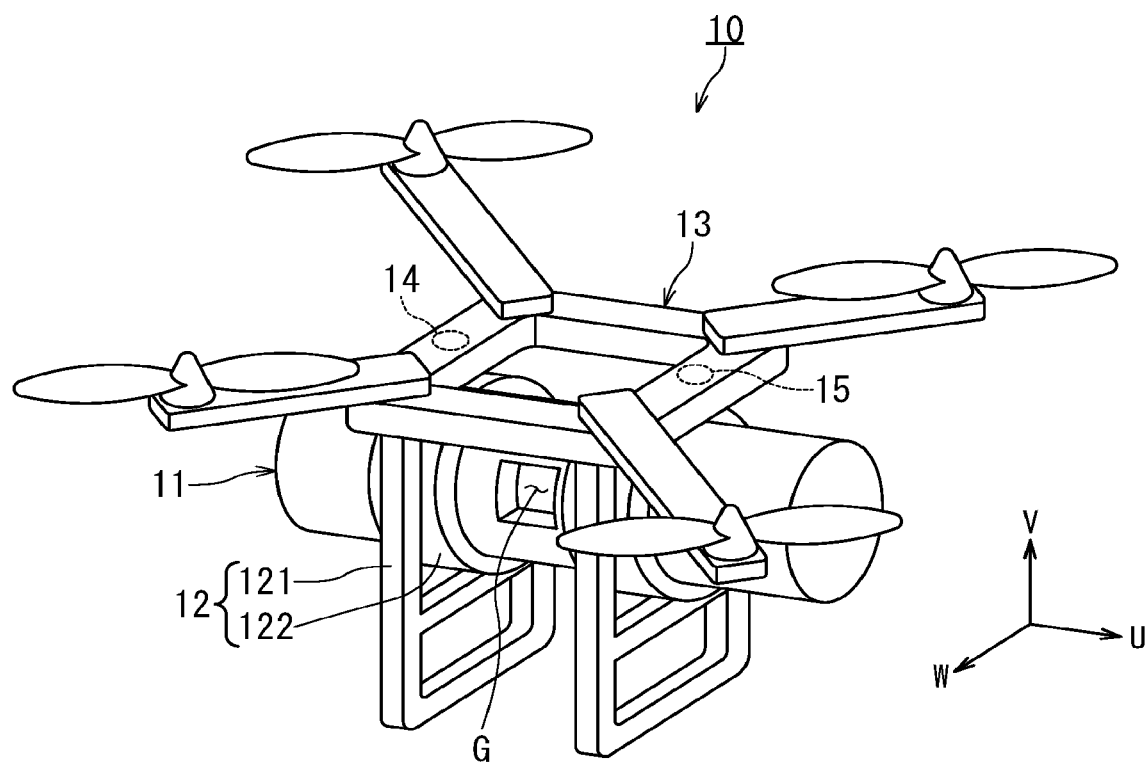
FIG. 1 is a schematic view showing a configuration of an X-ray tube holding apparatus according to an embodiment.

FIG. 1 is a schematic view showing a configuration of an X-ray tube holding apparatus according to an embodiment.

FIG. 1 shows an X-ray tube holding apparatus 10 according to an embodiment. The X-ray tube holding apparatus 10 includes an X-ray tube 11, a holding assembly 12 configured to hold the X-ray tube 11, and a flying object 13 equipped with the holding assembly 12.

The X-ray tube 11 receives power from a high-voltage power supply circuit 37 (shown in FIG. 3) and emits X-rays to a subject (e.g., a patient). A movable aperture assembly (or diaphragm assembly) (not shown) is provided near the opening G in the front portion of the X-ray tube 11. A radio quality adjusting filter (not shown) may be provided on the front surface of the X-ray tube 11 to adjust the quality of the X-rays generated by the X-ray tube 11.

The holding assembly 12 holds the X-ray tube 11. The holding assembly 12 includes a holding main body 121 and an angle changing member 122. The holding body 121 is connected to the flying object 13 as a leg of the flying object 13, which will be described later. Further, the holding main body 121 holds the angle changing member 122.

The angle changing member 122 holds the X-ray tube 11 such that the X-ray tube 11 can rotate around the body axis of the cylinder. With this configuration, the elevation/depression angle of X-ray emission from the X-ray tube 11 (hereinafter, simply referred to as "elevation/depression angle of the X-ray tube") is controlled. The angle changing member 122 for changing the elevation/depression angle of the X-ray tube 11 is not an essential configuration for the holding assembly 12. In a case of a standing posture imaging where the change the elevation/depression angle of the X-ray tube 11 is not required, the X-ray tube 11 may be fixed to the holding assembly 12 such that the elevation/depression angle of the X-ray tube 11 is in the horizontal direction. Further, in a case of a lying posture imaging where the change the elevation/depression angle of the X-ray tube 11 is not required, the X-ray tube 11 may be fixed to the holding assembly 12 such that the elevation/depression angle of the X-ray tube 11 is in the vertical direction.

In the specification, the direction parallel to the body axis of the cylinder of the X-ray tube 11 is defined as the U-axis direction of the X-ray tube 11, the vertical direction is defined as the V-axis direction of the X-ray tube 11, and the direction orthogonal to the U-axis direction and the V-axis direction is defined as the W-axis direction of the X-ray tube 11.

Figure 2A:
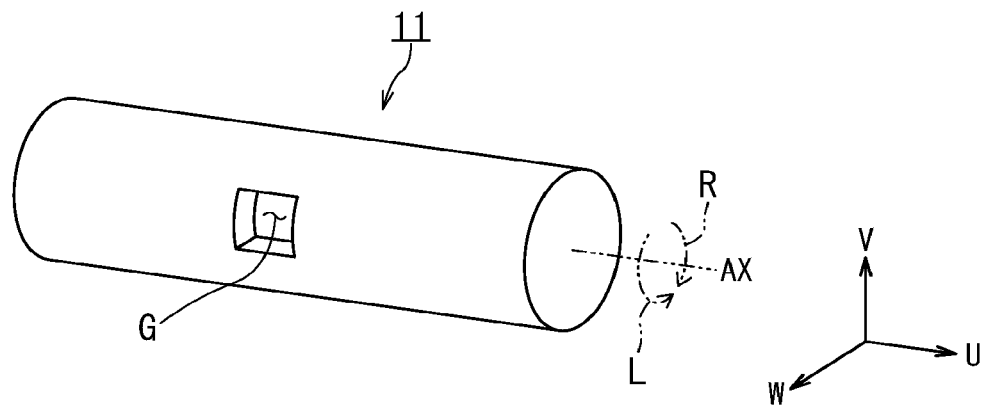
FIGS. 2A to 2C are diagrams for explaining the rotation of the X-ray tube provided in the X-ray tube holding apparatus according to the embodiment.
Figure 2B:
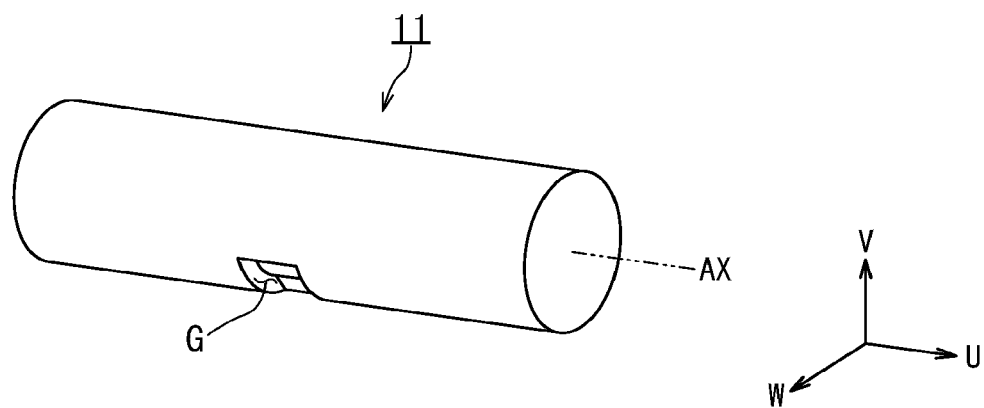
Figure 2C:
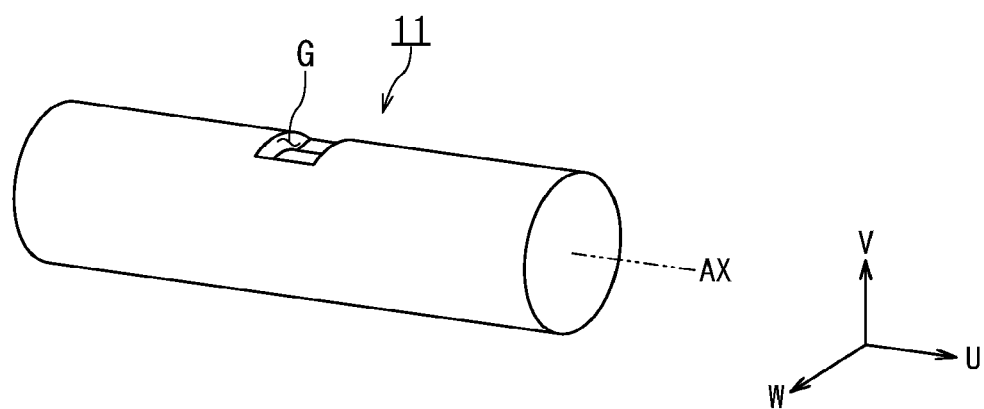

FIGS. 2A to 2C are diagrams for explaining the rotation of the X-ray tube 11 provided in the X-ray tube holding apparatus 10.

FIG. 2A shows the X-ray tube 11 extracted from the X-ray tube holding apparatus 10 shown in FIG. 1. An opening G is provided at the position of the X-ray emission of the X-ray tube 11. When the X-ray tube 11 rotates in the direction of the arrow L about the body axis AX from the state shown in FIG. 2A, the opening G moves downward as shown in FIG. 2B. On the other hand, when the X-ray tube 11 rotates in the direction of the arrow R about the body axis AX from the state shown in FIG. 2A, the opening G moves upward as shown in FIG. 2C. In this way, the angle changing member 122 can change the elevation/depression angle of the X-ray tube 11 by rotating the X-ray tube 11 around the body axis AX with respect to the holding assembly 12 (shown in FIG. 1). Hereinafter, unless otherwise specified, a case where the elevation/depression angle of the X-ray tube 11 is controlled will be described.

Returning to the description of FIG. 1, the flying object 13 means an unmanned aerial vehicle where no driver is board, so-called a "drone". The flying object 13 can fly by remote control (mainly wireless) by a control apparatus 30 (shown in FIG. 3) while holding the X-ray tube 11 and the holding assembly 12.

Further, the X-ray tube holding apparatus 10 may include position sensors 14 and 15 on the flying object 13. The position sensors 14 and 15 acquire each of its own position data. The case where two position sensors being provided on the flying object 13 will be described as an example, but the present invention is not limited to this case. The number of position sensors provided on the flying object 13 may be three or more. If it is necessary to control only the position of the X-ray focal point in the X-ray tube 11 (hereinafter, simply referred to as "the position of the X-ray tube") but not the azimuth angle of the emitted X-ray from the X-ray tube 11 (hereinafter, simply referred to as "the azimuth angle of X-ray tube"), the number of the position sensor may be one. The case where the control of the azimuth angle of the X-ray tube 11 is unnecessary is, for example, a case where the flying object 13 is not assumed to rotate about the V-axis direction during flight. Hereinafter, unless otherwise specified, a case where the position of the X-ray tube 11 and the azimuth angle of the X-ray tube 11 are both controlled will be described.

The position of the X-ray tube 11 and the azimuth angle of the X-ray tube 11 are acquired on the basis of the position data of the position sensors 14 and 15. The relative position between the position of the X-ray tube 11 and the combination of the position of the position sensor 14 and the position of the position sensor 15 is set in advance. Therefore, the position of the X-ray tube 11 is acquired based on the position data of the position sensors 14 and 15. Further, the relationship between the azimuth angle of the X-ray tube 11 and the combination of the position of the position sensor 14 and the position of the position sensor 15 is preset. Therefore, the azimuth angle of the X-ray tube 11 is acquired based on the combination of the position of the position sensors 14 and 15.

Further, the position data of the position sensors 14 and 15 is acquired by using an image sensor such as a multi-GNSS (Global Navigation Satellite System Profile), GPS (Global Positioning Satellite), a magnetic field sensor, and Kinect (registered trademark), or a combination thereof. When multi-GNSS or GPS is used, the position sensors 14 and 15 receive signals transmitted by radio waves from a plurality of satellites, thereby acquiring the position data of each of the position sensors 14 and 15 by measuring the transmission time.

When a magnetic field sensor is used, the magnetic field transmitter sequentially transmits a three-axis magnetic field which is sequentially received by the position sensors 14 and 15, thereby acquiring the position data of the position sensors 14 and 15, respectively.

Figure 3:
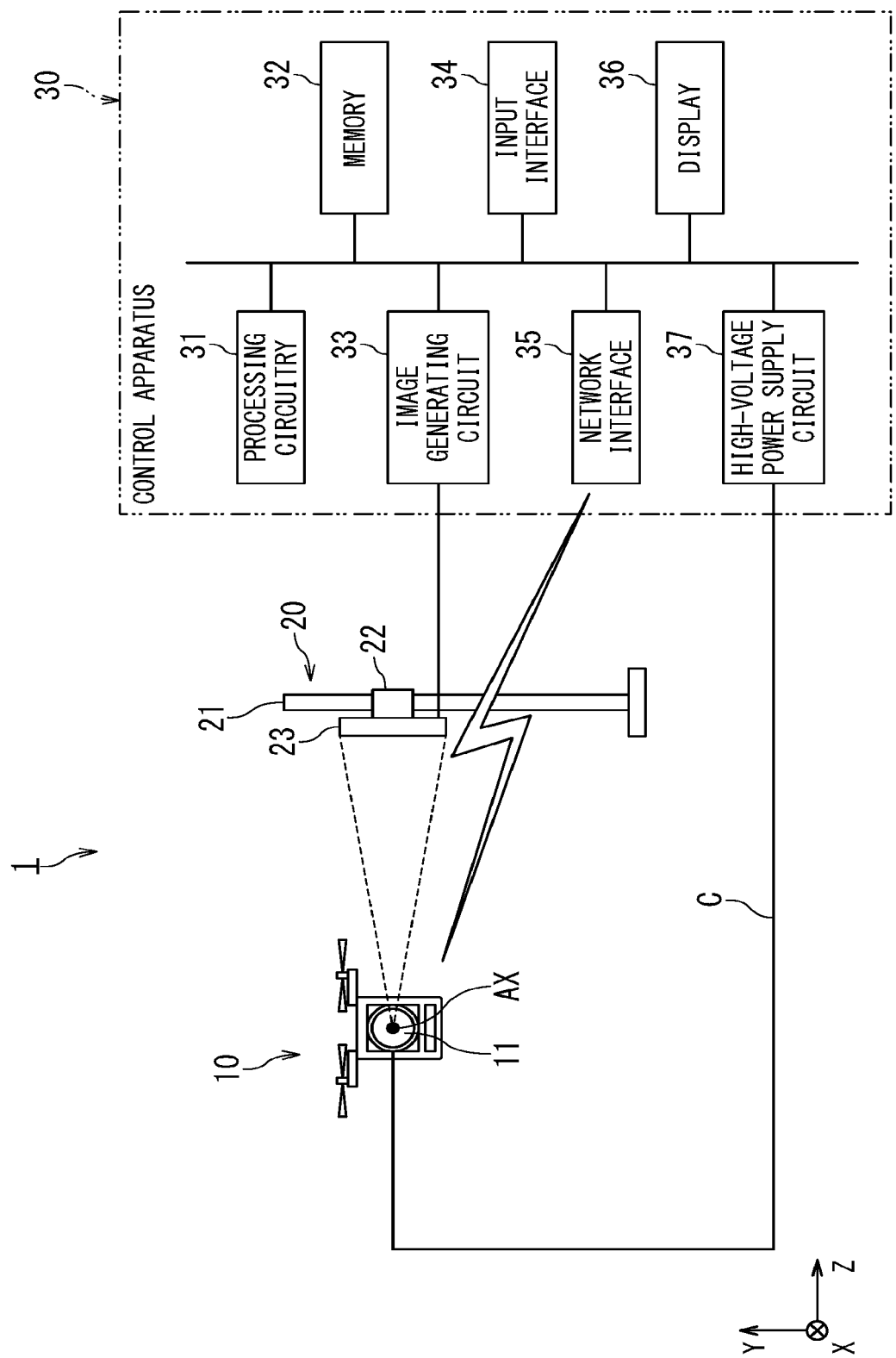
FIG. 3 is a schematic view showing a configuration of an X-ray imaging system including the X-ray tube holding apparatus according to the embodiment.

FIG. 3 is a schematic view showing a configuration of an X-ray imaging system including the X-ray tube holding apparatus 10.

FIG. 3 shows an X-ray imaging system 1. The X-ray imaging system 1 includes the X-ray tube holding apparatus 10 shown in FIG. 1, a standing posture imaging stand 20, and a control apparatus (e.g., a console) 30.

FIG. 3 shows a case where the U-axis of the X-ray tube (shown in FIG. 1), that is parallel to the body axis AX, of the X-ray tube holding apparatus 10 is parallel to the horizontal axis of the standing posture detector 23, that is the X-axis, which will be described later. It is assumed that the V-axis of the X-ray tube 11 always coincides with the vertical axis (vertical direction) of the standing posture detector 23, that is, the Y-axis.

The X-ray tube 11 receives power from a high-voltage power supply circuit 37 while hovering using the flying object 13. The tube 11 emits X-rays to an examination region of the patient placed in front of the standing posture imaging stand 20. A movable aperture assembly (not shown) is provided at the front portion of the X-ray tube 11. The movable aperture assembly is an X-ray emission port of the X-ray tube 11 and has slidable blades made of materials that shields X-rays. Under the control of the processing circuitry 31, the movable aperture assembly can change the X-ray spread angle by opening and closing the X-ray emission port. A radiation quality adjusting filter (not shown) may be provided on the front surface of the X-ray tube 11 to adjust the quality of the X-rays generated by the X-ray tube 11.

By controlling the flight of the flying object 13 using the control apparatus 30, the X-ray tube 11 of the X-ray tube holding apparatus 10 can be moved to a predetermined position. For example, the flying object 13 may be automatically steered such that the X-ray tube 11 matches the position and azimuth angle set by the control apparatus 30.

The standing posture imaging stand 20 is arranged at a position facing the X-ray tube 11. The standing posture imaging stand 20 includes a stand 21, a moving assembly 22, and an X-ray detector for the standing posture imaging (hereinafter, referred to as "standing posture detector") 23. The stand 21 holds the standing posture detector 23 through the moving assembly 22. The moving assembly 22 slides the standing posture detector 23 in the Y-axis direction along the stand 21.

The standing posture detector 23 includes, for example, a flat panel detector (FPD). The standing posture detector 23 is an X-ray detector for radiography, fluoroscopy, or a combination thereof. The standing posture detector 23 includes detection elements arranged in two dimensions. A grid (not shown) may be provided on the front surface of the standing posture detector 23 (e.g., the X-ray incident surface). It is desired that the grid absorbs scattered radiation incident on the standing posture detector 23 to improve the contrast of the X-ray image. Therefore, grid plates made of lead or the like having a large X-ray absorption effect along with aluminum, wood, etc., that penetrate easily are alternately arranged on the grid. In the specification, among the X-axis, Y-axis, and Z-axis of the three-dimensional system, the height direction of the stand 21 is defined as the Y-axis. The left-right direction of the patient standing in front of the standing posture imaging stand 20 is defined as the X-axis direction. The direction orthogonal to the X-axis direction and the Y-axis direction is defined as the Z-axis direction.

The standing posture detector 23 may include an analog to digital (A/D) conversion circuit or the like in addition to the FPD. The A/D conversion circuit inputs an analog signal (video signal) output from the FPD, converts it into a digital image signal, and outputs it to the control apparatus 30.

The control apparatus 30 includes a function of controlling the position and azimuth angle of the X-ray tube 11 by controlling the flight of the flying object 13 of the X-ray tube holding apparatus 10, a function of controlling the elevation/depression angle of the X-ray tube 11 by controlling the operation of the angle changing member 122 of the X-ray tube holding apparatus 10, and a function of controlling X-ray imaging. The control apparatus 30 includes processing circuitry 31, a memory 32, an image generating circuit 33, an input interface 34, a network interface 35, a display 36, and a high-voltage power supply circuit 37. The image generating circuit 33 is configured by an application specific integrated circuit (ASIC) or the like. However, the present invention is not limited to this case, and all or part of the functions of the image generating circuit 33 may be realized by the processing circuitry 31 executing a program.

The processing circuitry 31 controls whole operations of the control apparatus 30. The processing circuitry 31 may refer to a processor such as a dedicated or general-purpose central processing unit (CPU), a microprocessor unit (MPU), a graphics processing unit (GPU), or the like. The processing circuitry 31 may refer to an ASIC, a programmable logic device, or the like. The programmable logic device is, for example, a simple programmable logic device (SPLD), a complex programmable logic device (CPLD), and a field programmable gate array (FPGA).

Further, the processing circuitry 31 may be constituted by a single circuit or a combination of independent circuit elements. In the latter case, the memory 32 may be provided individually for each circuit element, or a single memory 32 may store programs corresponding to the functions of the circuit elements.

The memory 32 is constituted by a semiconductor memory element such as a random-access memory (RAM), a flash memory, a hard disk, an optical disk, or the like. The memory 32 may be constituted by a portable medium such as a universal serial bus (USB) memory and a digital video disk (DVD). The memory 32 stores various processing programs (including an operating system (OS) and the like besides the application program) used in the processing circuitry 31 and data necessary for executing the programs. In addition, the OS may include a graphical user interface (GUI) which allows the operator to frequently use graphics to display information on the display 36 to the operator and can perform basic operations using the input interface 34. The memory 32 is an example of a storage unit.

Under the control of the processing circuitry 31, the image generating circuit 33 performs logarithmic conversion processing (LOG processing) on transparent data output from the A/D conversion circuit (not shown) of the standing posture detector 23 (or lying posture detector 43), performs addition processing as needed, and generates X-ray image data. Further, the image generating circuit 33 performs image processing on the generated X-ray image data under the control of the processing circuitry 31. Examples of the image processing include enlargement/gradation/spatial filter processing of data, minimum/maximum value tracing processing of data accumulated in time series, and addition processing for removing noise.

The image generating circuit 33 stores the generated image data in a storage such as a memory 32. The image generating circuit 33 is an example of an image generating unit.

The input interface 34 includes an input device operable by an operator, and a circuit for inputting a signal from the input device. The input device may be a trackball, a switch, a mouse, a keyboard, a touch pad for performing an input operation by touching an operation surface, a touch screen in which a display screen and a touch pad are integrated, a non-contact input circuit using an optical sensor, an audio input circuit, and the like. When the input device is operated by the operator, the input interface 34 generates an input signal corresponding to the operation and outputs it to the processing circuitry 31. The input interface 34 is an example of an input unit.

The network interface 35 implements various information communication protocols according to the network form. The network interface 35 connects the X-ray imaging apparatus 1 and other apparatuses such as the external image server (not shown) according to these various protocols. An electrical connection or the like via an electronic network is applied to this connection. In the present embodiment, the electronic network refers to an entire information communication network using telecommunications technology. The electronic network includes a wired/wireless hospital backbone local area network (LAN) and the Internet network, as well as a telephone communication line network, an optical fiber communication network, a cable communication network, a satellite communication network, or the like. The network interface 35 is an example of a network connecting unit.

The display 36 displays various information. For example, the display 36 outputs image data generated by the image generating circuit 33, pseudo image data to be described later, a graphical user interface (GUI) for receiving various operations from the operator, and the like. The display 36 may be a liquid crystal display, a cathode ray tube (CRT) display, an organic light emitting diode (OLED) display, or the like. The display 36 is an example of a display unit.

The high-voltage power supply circuit 37 boosts the voltage by using a commercial power supply as an input, and supplies high-voltage power to the X-ray tube 11 of the X-ray tube holding apparatus 10 via the cable C under the control of the processing circuitry 31.

Subsequently, functions of the control apparatus 30 of the X-ray imaging system 1 will be described.

Figure 4:
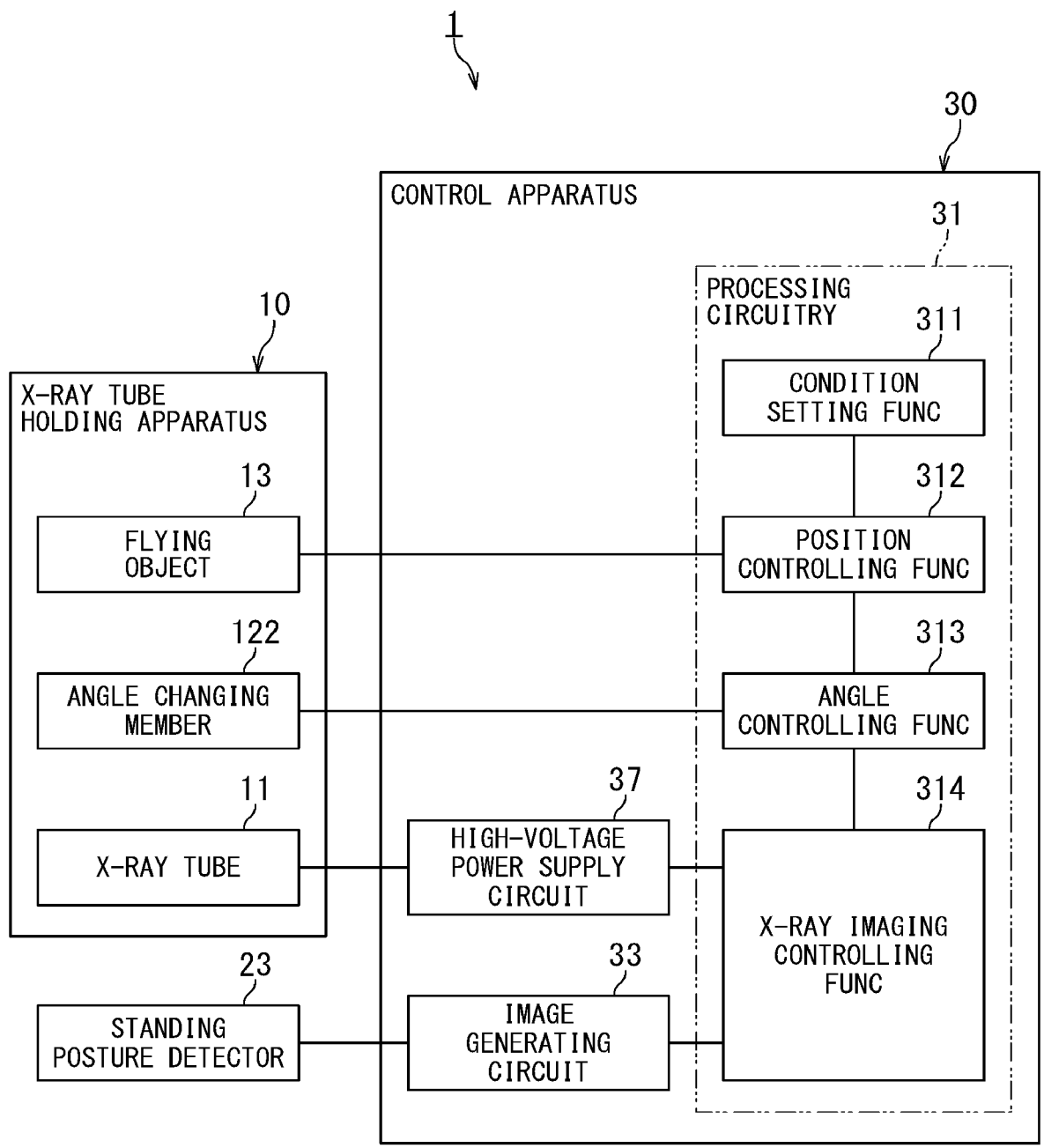
FIG. 4 is a block diagram showing an example of functions of the control apparatus provided in the X-ray tube holding apparatus according to the embodiment.

FIG. 4 is a block diagram showing an example of functions of the control apparatus 30.

As shown in FIG. 4, the processing circuitry 31 reads and executes a computer program stored in the memory 32 or directly embedded in the processing circuitry 31, thereby realizing a condition setting function 311, a position controlling function 312, an angle controlling function 313, and an X-ray imaging controlling function 314. Hereinafter, the case where the functions 311 to 314 function as software will be described as an example, but all or a part of the functions 311 to 314 may be realized by a circuit such as an ASIC.

Further, the functions 311 to 313 may be provided in a computer different from the control apparatus 30 having the X-ray imaging controlling function 314, for example, a doublet type computer or the like.

The condition setting function 311 includes a function of setting an imaging condition such as SID (that is, Z coordinate) according to the input via the input interface 34 or the condition included in an examination order. For example, when X-rays are emitted to the standing posture detector 23 from the front, the X-axis coordinates of the three-dimensional coordinates [X, Y, Z] of the X-ray tube 11 match the X-axis coordinates of the center position of the standing posture detector 23, the Y-axis coordinates of the three-dimensional coordinates [X, Y, Z] of the X-ray tube 11 match the Y-axis coordinates of the center position of the standing posture detector 23, the Z-axis coordinates of the three-dimensional coordinates [X, Y, Z] of the X-ray tube 11 correspond to the difference between the Z-axis coordinates of the center position of the standing detector 23 and the SID. It is assumed that the position of the standing posture detector 23 has been acquired in advance. The condition setting function 311 is an example of a condition setting unit.

The position controlling function 312 includes a function of wirelessly controlling the position and azimuth angle of the X-ray tube 11 of the X-ray tube holding apparatus 10. The position controlling function 312 positions the current position and azimuth angle of the X-ray tube 11 as well as the target position and azimuth angle of the X-ray tube 11 set by the condition setting function 311, and sets the flight route of the X-ray tube holding apparatus 10. For example, when X-rays are emitted to the standing posture detector 23 from the front, the position controlling function 312 controls the direction of the flying object 13 such that the body axis AX of the X-ray tube 11 is parallel to the X-axis so as to control the azimuth angle of the X-ray tube 11. That is, the position controlling function 312 controls the flight of the flying object 13 such that the X-ray tube 11 faces the standing posture detector 23. On the other hand, the angle controlling function 313 controls the orientation of the flying object 13 so as to control the azimuth angle of the X-ray tube 11, which enables to emit X-rays to the standing posture detector 23 from the left side or from the right side. The position controlling function 312 is an example of a position controlling unit.

The angle controlling function 313 includes a function of wirelessly controlling the rotation of the X-ray tube 11 of the X-ray tube holding apparatus 10. For example, when X-rays are emitted to the standing posture detector 23 from the front, the angle controlling function 313 controls the elevation/depression angle of the X-ray tube 11 (shown in FIG. 2A) such that a line connecting the X-ray focal point of the X-ray tube 11 and the opening G is parallel to the W-axis. That is, the angle controlling function 313 controls the operation of the angle changing member 122 such that the X-ray tube 11 faces the standing posture detector 23. On the other hand, the angle controlling function 313 enables to emit X-rays to the standing posture detector 23 from above or below by controlling the elevation/depression angle of the X-ray tube 11 (shown in FIGS. 2B and 2C). The angle controlling function 313 is an example of an angle controlling unit.

The X-ray imaging controlling function 314 includes a function of wirelessly controlling the operation of the X-ray tube 11 and the standing posture detector 23 while the X-ray tube holding apparatus 10 is hovering, and supplying power to the X-ray tube 11 from the high voltage power supply circuit 37 via the cable C, thereby controlling X-ray imaging of a patient's examination region located in front of the standing posture detector 23. The X-ray imaging controlling function 314 is an example of an X-ray imaging controlling unit.

X-ray emission is roughly classified into geography and fluoroscopy. In geography, X-rays are emitted with a relatively high tube current. On the other hand, in fluoroscopy, X-rays are emitted with a relatively low tube current. Further, fluoroscopy is roughly classified into continuous fluoroscopy and pulse fluoroscopy. Unlike continuous fluoroscopy, pulse fluoroscopy means a fluoroscopy method in which X-ray pulses are intermittently and repeatedly irradiated. Compared with the continuous fluoroscopy, the continuity (frame rate) of fluoroscopic images using pulse fluoroscopy is slightly inferior, but the exposure dose to the patient can be suppressed.

Subsequently, a method of controlling X-ray imaging in the X-ray imaging system 1 will be described.

Figure 5:
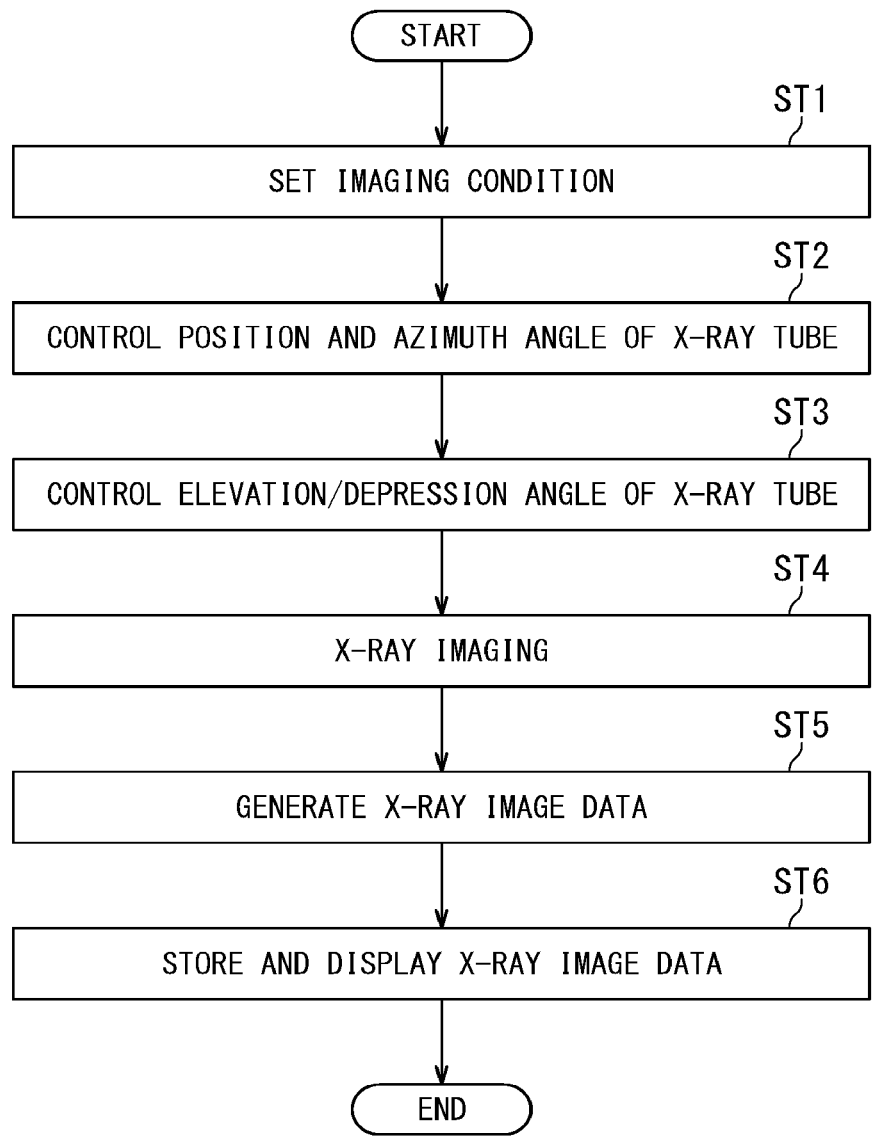
FIG. 5 is a diagram showing a control method of an X-ray imaging as a flowchart in the X-ray imaging system according to the embodiment.

FIG. 5 is a diagram showing a control method of an X-ray imaging as a flowchart. In FIG. 5, reference numerals with numbers attached to "ST" indicate each step of the flowchart.

The condition setting function 311 sets an imaging condition such as SID according to the input via the input interface 34 or the condition included in an examination order (step ST1). The position controlling function 312 controls the flight of the flying object 13 of the X-ray tube holding apparatus 10, thereby setting the position and azimuth angle of the X-ray tube 11 such that the position and azimuth angle are based on the SID set in step ST1 (step ST2). In step ST2, the position controlling function 312 positions the current position and azimuth angle of the X-ray tube 11 and the target position and azimuth angle of the X-ray tube 11 set by the condition setting function 311, thereby setting the flight route of the X-ray tube holding apparatus 10. The X-ray tube holding apparatus 10 flies along the flight route and sets the position and azimuth angle of the X-ray tube 11.

In step ST2, when an obstacle such as a device exists in the optimum flight route toward a predetermined position, the position controlling function 312 may change the flight route so as to avoid the obstacle. The position of the obstacle may be set in advance or may be detected by a position sensor such as an image sensor. In such manner, the risk of the X-ray tube holding apparatus 10 colliding with an obstacle can be avoided. Thought the position controlling function 312 generally controls the position of the X-ray tube 11 to be in front of the standing posture detector 23 and to emit the X-ray from the front, X-rays may be emitted to the standing posture detector 23 from the left side or from the right side. In this case, the position controlling function 312 controls the X-ray coordinates of the position of the X-ray tube 11 and controls the operation of the movable aperture assembly (not shown) so as to control the azimuth angle of the X-ray tube 11.

The angle controlling function 313 controls the rotation of the X-ray tube 11 of the X-ray tube holding apparatus 10 while the X-ray tube holding apparatus 10 is hovering in step ST2, thereby setting the elevation/depression angle of the X-ray tube 11 (step ST3). Though the angle controlling function 313 generally controls the position of the X-ray tube 11 to be in front of the standing posture detector 23 and to emit X-rays from the front, X-rays may be emitted to the standing posture detector 23 from above or below. In this case, the angle controlling function 313 controls the Y-axis coordinates of the position of the X-ray tube 11, and controls the movable aperture assembly (not shown) so as to control the elevation/depression angle of the X-ray tube 11.

The X-ray imaging controlling function 314 controls the operations of the X-ray tube 11, the high-voltage power supply circuit 37, the standing posture detector 23, and the like while the X-ray tube holding apparatus 10 is hovering in step ST2, thereby performing X-ray imaging of the patient's examination region located in front of the standing posture detector 23 (step ST4).

The image generating circuit 33 generates X-ray image data based on transparent data acquired by the X-ray imaging in step ST4 (step ST5). The X-ray imaging controlling function 314 stores the X-ray image data generated in step ST5 in the memory 32 and displays it on the display 36 (step ST6).

As described above, according to the X-ray tube holding apparatus 10 shown in FIG. 1, the movable range of the X-ray tube 11 is not limited by ceiling rails or an arm that holds the X-ray tube 11. Therefore, it is possible to provide the X-ray tube 11 having a high degree of arrangement freedom. Further, if the X-ray tube holding apparatus 10 is applied to the X-ray imaging system 1, it is possible to perform the X-ray imaging with a large SID.

In addition to apply the X-ray tube holding apparatus 10 to a general X-ray imaging system, it is also possible to apply the X-ray tube holding apparatus 10 to a system for rounds in the hospital Further, since the X-ray imaging system 1 does not require ceiling construction for holding the X-ray tube as in the conventional X-ray imaging system, the preparation time for installation can be shortened.

The case where the X-ray tube holding apparatus 10 shown in FIG. 1 being applied to the X-ray imaging system 1 related to the standing posture imaging has been described as an example. However, the present invention is not limited to that case. For example, in the present invention, the X-ray tube holding apparatus 10 shown in FIG. 1 can also be applied to an X-ray imaging system related to the lying posture imaging. The case will be described below.

Figure 6:
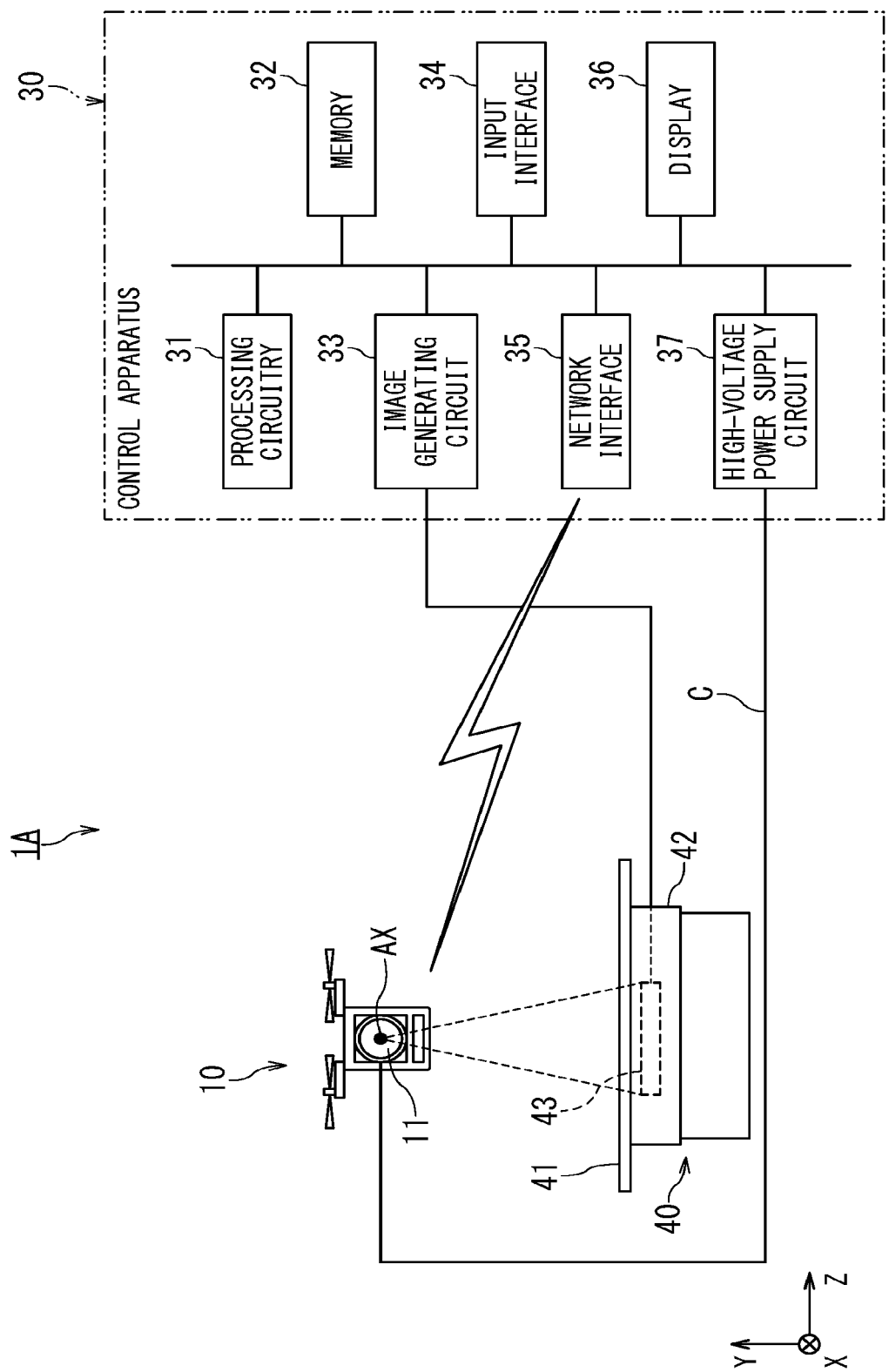
FIG. 6 is a schematic view showing a configuration of the X-ray imaging system including the X-ray tube holding apparatus according to the embodiment.

FIG. 6 is a schematic view showing a configuration of the X-ray imaging system including the X-ray tube holding apparatus 10.

FIG. 6 shows an X-ray imaging system 1A. The X-ray imaging system 1A includes an X-ray tube holding apparatus 10 and the control apparatus 30 shown in FIG. 1, and a lying posture imaging table 40.

The lying posture imaging table 40 is arranged sideways such that the patient can be placed on it, and is arranged in a manner that X-rays from the X-ray tube 11 can be detected. The lying posture imaging table 40 includes a table-top 41, a bed 42, and an X-ray detector for the lying posture imaging (hereinafter, referred to as "lying posture detector") 43.

The table-top 41 has a plate-like shape arranged on the upper side of the lying posture imaging table 40, and the patient is placed on the upper plate.

The bed 42 supports the table-top 41 upward. The bed 42 slides the table-top 41 in the vertical direction, the horizontal direction, and the front-rear direction under the control of the processing circuitry 31 of the control apparatus 30.

The lying posture detector 43 includes, for example, the FPD, similar to the standing posture detector 23 (shown in FIG. 3). The lying posture detector 43 is an X-ray detector for geography, fluoroscopy, or a combination thereof. The lying posture detector 43 includes detection elements arranged in two dimensions. A grid (not shown) may be provided on the front surface of the lying posture detector 43 (e.g., the X-ray incident surface) as on the front surface of the standing posture detector 23.

The lying posture detector 43 may include an A/D conversion circuit or the like in addition to the FPD. The A/D conversion circuit inputs an analog signal (video signal) output from the FPD, converts it into a digital image signal, and outputs it to the control apparatus 30.

In the X-ray imaging system 1A shown in FIG. 6, the same members as those of the X-ray imaging system 1 shown in FIG. 3 are designated by the same reference numerals, and the description thereof will be omitted. Further, since the function of the X-ray imaging system 1A is equivalent to the function of the X-ray imaging system 1 shown in FIG. 4, the description thereof will be omitted. Further, since the control method of X-ray imaging by the X-ray imaging system 1A is the same as the control method of X-ray imaging by the X-ray imaging system 1 shown in FIG. 5, the description thereof will be omitted.

As described above, if the X-ray tube holding apparatus 10 shown in FIG. 1 is applied to the X-ray imaging system 1A, it is possible to perform X-ray imaging with a large SID.

FIRST MODIFIED EXAMPLE

According to the X-ray imaging system 1A shown in FIG. 6, tomosynthesis imaging can also be performed. A case will be described with reference to FIG. 7.

Figure 7:
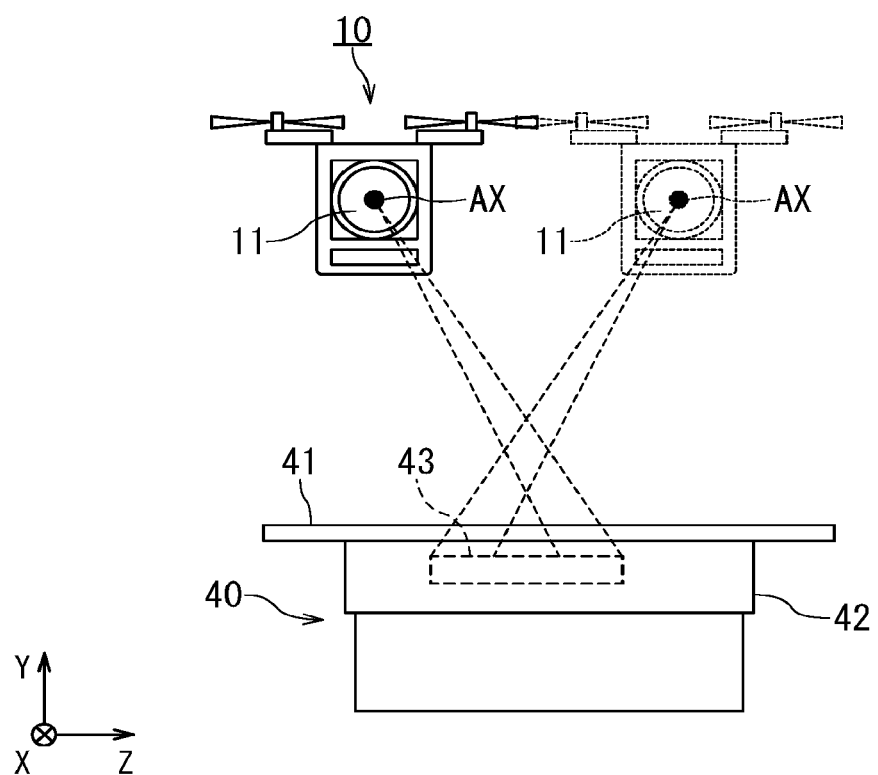
FIG. 7 is a diagram for explaining tomosynthesis imaging in the X-ray imaging system according to the embodiment.

FIG. 7 is a diagram for explaining tomosynthesis imaging in the X-ray imaging system 1A.

FIG. 7 shows the X-ray tube holding apparatus 10 and the lying posture imaging table 40. The X-ray tube holding apparatus 10, that is, the X-ray tube 11 is linearly slid and moved in the Z-axis direction, and the elevation/depression angle of the X-ray tube 11 is under control, while the tomosynthesis imaging is performed. Further, the X-ray tube 11 is not limited to the case where the X-ray tube 11 is linearly slid in the Z-axis direction. The tomosynthesis imaging may be performed by moving the X-ray tube 11 in the arc direction centered on the midpoint between the focal position of the X-ray tube 11 and the center of the lying posture detector 43. Further, the lying posture detector 43 is not limited to a fixed one. Tomosynthesis imaging may be performed by moving the lying posture detector 43 in the negative direction of the Z-axis in accordance with the movement of the X-ray tube 11 in the positive direction of the Z-axis.

As described above, according to the X-ray imaging system 1A to which the X-ray tube holding apparatus 10 is applied, when the X-ray tube moves in a constant straight line or in an arc-like trajectory as in the tomosynthesis imaging, situations where the imaging cannot be performed due to obstacles such as curtain rails in the examination room can be avoided. According to the X-ray imaging system 1A, it is possible to avoid the curtain rails and perform imaging in an orbit of tomosynthesis close to what is planned. That is, according to the X-ray imaging system 1A, it is possible to perform imaging in the trajectory of the X-ray tube that cannot not be done using the conventional system, thereby the range of examination can be expanded.

Second Modified Example

Not only one X-ray tube holding apparatus 10 but multiple ones may be applied to the X-ray imaging systems 1 and 1A. By sequentially exchanging and using the multiple of X-ray tube holding apparatus 10, it is possible to continuously perform imaging even with the X-ray tube 11 having a small heat unit (HU). Considering that the X-ray tube 11 is flown by using the flying object 13, it is preferable to make the X-ray tube 11 smaller and lighter. Accordingly, it is difficult to adopt an X-ray tube 11 equipped with a rotating anode that rotates the anode, while a fixed anode is more desirable. However, in the case of using an X-ray tube having a fixed anode, even under the same X-ray conditions, it may become too hot quickly and disable the imaging.

Therefore, one or more X-ray tube holding apparatuses 10 can be used for backup. The control apparatus 30 controls the operation of the active X-ray tube holding apparatus 10 among the multiple X-ray tube holding apparatuses 10 to acquire X-ray image data. By doing so, when the X-ray tube 11 of the first X-ray tube holding apparatus 10 becomes unable to perform imaging, it is possible to continue imaging using other X-ray tube holding apparatus 10. The X-ray imaging controlling function 314 controls the operation of the two X-ray tube holding apparatuses 10, thereby acquiring X-ray image data for stereoscopic vision by having the two X-ray tubes 11 corresponding to the respective two X-ray tube holding apparatuses 10 to emit X-rays alternately.

THIRD MODIFIED EXAMPLE

The X-ray imaging systems 1 and 1A may include a cable support apparatus 50. The cable support apparatus 50 supports the cable, which supplies power from the high-voltage power supply circuit 37 to the X-ray tube 11, so the cable will not loosen.

Figure 8:
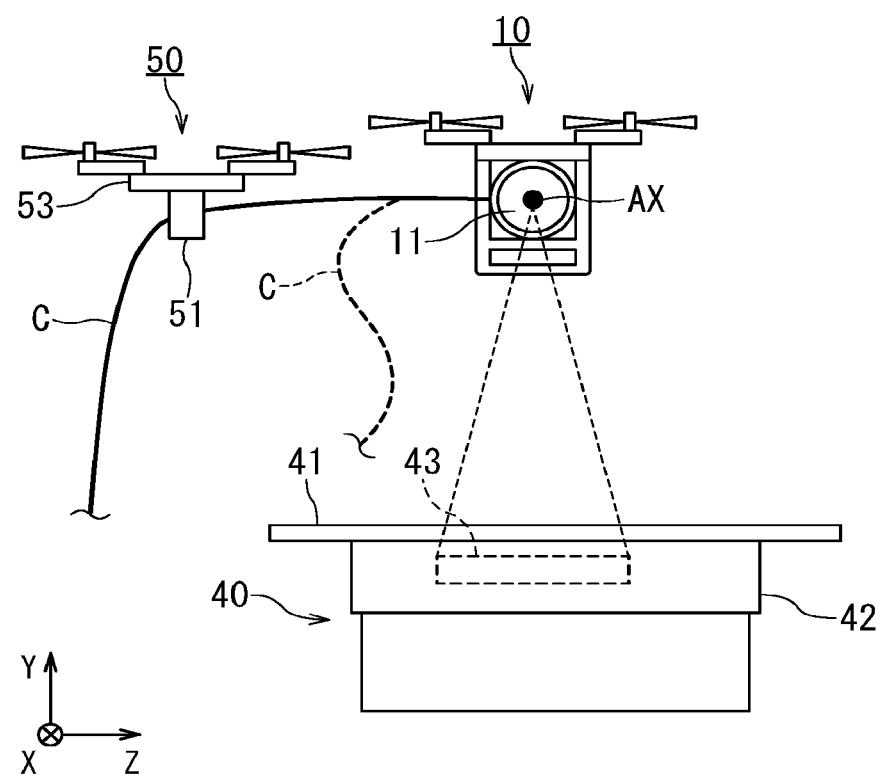
FIG. 8 is a diagram for explaining a support of a cable by a cable support apparatus in the X-ray imaging system according to the embodiment.

FIG. 8 is a diagram for explaining a support to the cable by the cable support apparatus 50 in the X-ray imaging systems 1 and 1A.

FIG. 8 shows an X-ray tube holding apparatus 10, a lying posture imaging table 40, and a cable support apparatus 50. The cable support apparatus 50 includes a flying object 53 having the same configuration as the flying object 13 (shown in FIG. 1) of the X-ray tube holding apparatus 10, and a support assembly 51 (e.g., a pulley). The support assembly 51 is provided below the flying object 53 and supports the cable C that supplies electric power from the high-voltage power supply circuit 37 to the X-ray tube 11. It is desirable that the cable support apparatus 50 moves following the movement of the X-ray tube holding apparatus 10.

Since the X-ray tube holding apparatus 10 can fly freely, it is assumed that the cable C may hang down on the patient on the lying posture imaging table 40 (thick broken line in FIG. 8). To deal with this issue, the cable support apparatus 50 flown by the flying object 53 supports the cable C, and the position controlling function 312 wirelessly controls the position and azimuth angle of the X-ray tube holding apparatus 10, while wirelessly controlling the position of the cable support apparatus 50 so as to follow the position of the X-ray tube holding apparatus 10. In such manner, it is possible to prevent the cable C from hanging down on the patient on the lying posture imaging table 40. In addition, instead of using the cable support apparatus 50, the flying object 13 of the X-ray tube holding apparatus 10 may be further provided with an arm for supporting the cable C. The same effect can be easily acquired as the case using the cable support apparatus 50.

FOURTH MODIFIED EXAMPLE

In the X-ray imaging systems 1 and 1A, the X-ray imaging controlling function 314 may control the emission of X-rays from the X-ray tube 11 according to the flight state of the flying object 13. If the image is not taken when the flying object 13 is in a stable flight state, that is, when the X-ray tube 11 is stationary, the acquired X-ray image may be blurred. Therefore, the X-ray imaging controlling function 314 controls the operation of the X-ray tube 11 via the high-voltage power supply circuit 37 so as to perform imaging when the X-ray tube 11 is stationary or in a stable flight state. For example, the X-ray imaging controlling function 314 can recognize the stationary state and the stable state of the X-ray tube 11 by measuring the movement amount per hour according to the position data of the flying object 13, which will prevent blurry X-ray image due to the movement of the X-ray tube 11.

FIFTH MODIFIED EXAMPLE

The movable aperture assembly (not shown) mounted on the flying object 13 is preferably lightweight in consideration of the maximum load weight of the flying object 13. Therefore, it is assumed that the function of the movable aperture assembly mounted on the flying object 13 is limited. For example, from the viewpoint of weight, the flying object 13 cannot be equipped with a complicated aperture assembly that operates asymmetrically in the vertical and horizontal directions. Therefore, the X-ray imaging system 1A may be provided with a landing assembly 44 of the X-ray tube holding apparatus 10 equipped with an additional movable aperture assembly.

Figure 9A:
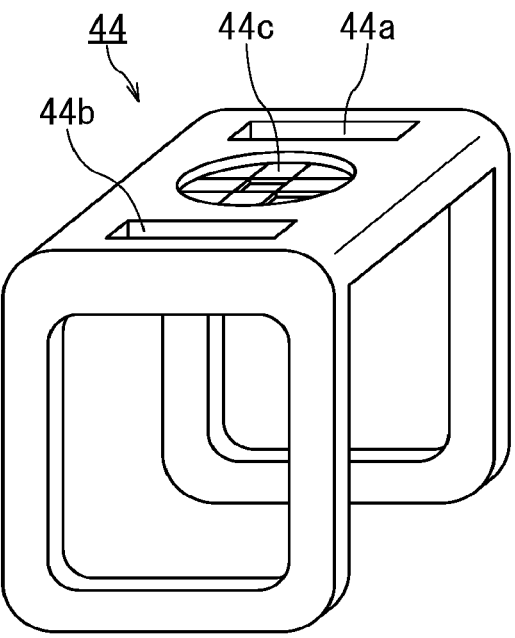
FIG. 9A is a diagram showing a configuration example of a landing assembly of the X-ray tube holding apparatus according to the embodiment.
Figure 9B:
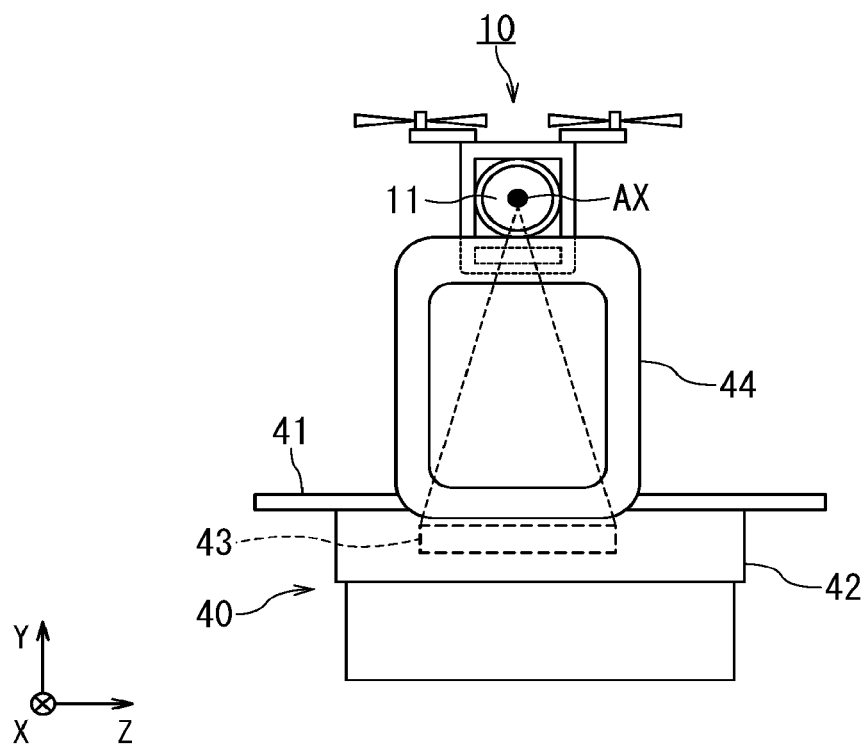
FIG. 9B is a diagram showing an arrangement example of the landing assembly.

FIG. 9A is a diagram showing a configuration example of the landing assembly 44 of the X-ray tube holding apparatus 10. FIG. 9B is a diagram showing an arrangement example of the landing assembly 44.

As shown in FIG. 9A, the landing assembly 44 includes landing grooves 44a and 44b for the X-ray tube holding apparatus 10 and a movable aperture assembly 44c. As shown in FIG. 9B, the legs of the X-ray tube holding apparatus 10 touch the landing grooves 44a and 44b of the landing assembly 44, which is fixed to the bed 42 (or the table-top 41). Thereby, the X-ray tube holding apparatus 10 is aligned with and fixed to the lying posture imaging table 40.

In the examination such as urinary examination using an X-ray TV system, using only the lower side of the X-ray top-left is desired, thereby applying a movable aperture assembly having blades that operate asymmetrically for the examination may be preferable. In this case, the landing assembly 44 having the desired movable aperture assembly 44c is provided on the lying posture imaging table 40, and the position controlling function 312 controls the flight of the flying object 13 such that the X-ray tube holding apparatus 10 lands at a predetermined position of the landing assembly 44. In such manner, it is possible to perform imaging using the desired movable aperture assembly 44c.

SIXTH MODIFIED EXAMPLE

The X-ray tube holding apparatus 10 shown in FIG. 1 does not include a high-voltage power supply circuit. On the other hand, the control apparatus 30 includes the high-voltage power supply circuit 37, and the X-ray tube 11 of the X-ray tube holding apparatus 10 receives electric power supply from the high-voltage power supply circuit 37 of the control apparatus 30. However, it is not limited to such a configuration. The X-ray tube holding apparatus that holds the X-ray tube 11 may include a high-voltage power supply circuit.

Figure 10:
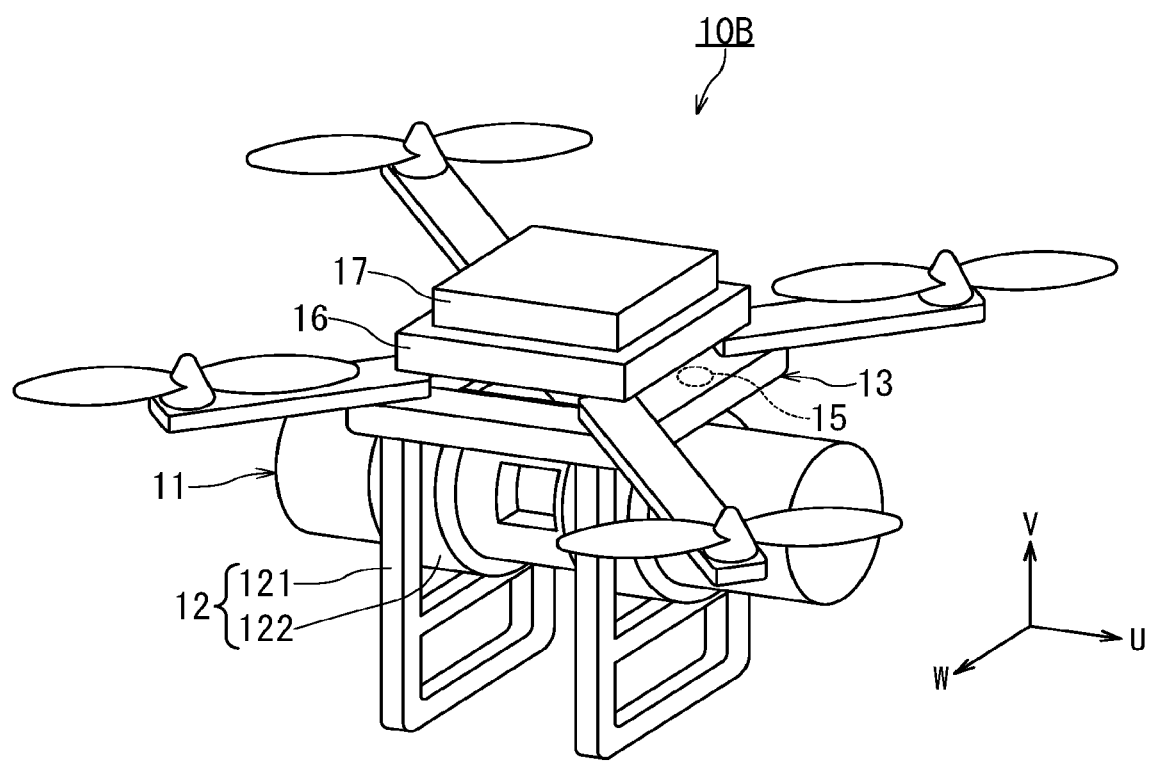
FIG. 10 is a schematic view showing a configuration of an X-ray tube holding apparatus according to the sixth modified example.

FIG. 10 is a schematic view showing a configuration of the X-ray tube holding apparatus according to the sixth modified example.

FIG. 10 shows an X-ray tube holding apparatus 10B according to the sixth modified example. The X-ray tube holding apparatus 10B includes an X-ray tube 11, a holding assembly 12, a flying object 13, a high-voltage power supply circuit 16, and a storage battery (battery) 17.

The high-voltage power supply circuit 16 boosts the voltage by using the power supply of the battery 17 as an input, and supplies high-voltage power to the X-ray tube 11 of the X-ray tube holding apparatus 10B under the control of the processing circuitry 31.

In the X-ray tube holding apparatus 10B shown in FIG. 10, the same members as those of the X-ray tube holding apparatus 10 shown in FIG. 1 are designated by the same reference numerals, and the description thereof will be omitted.

Figure 11:
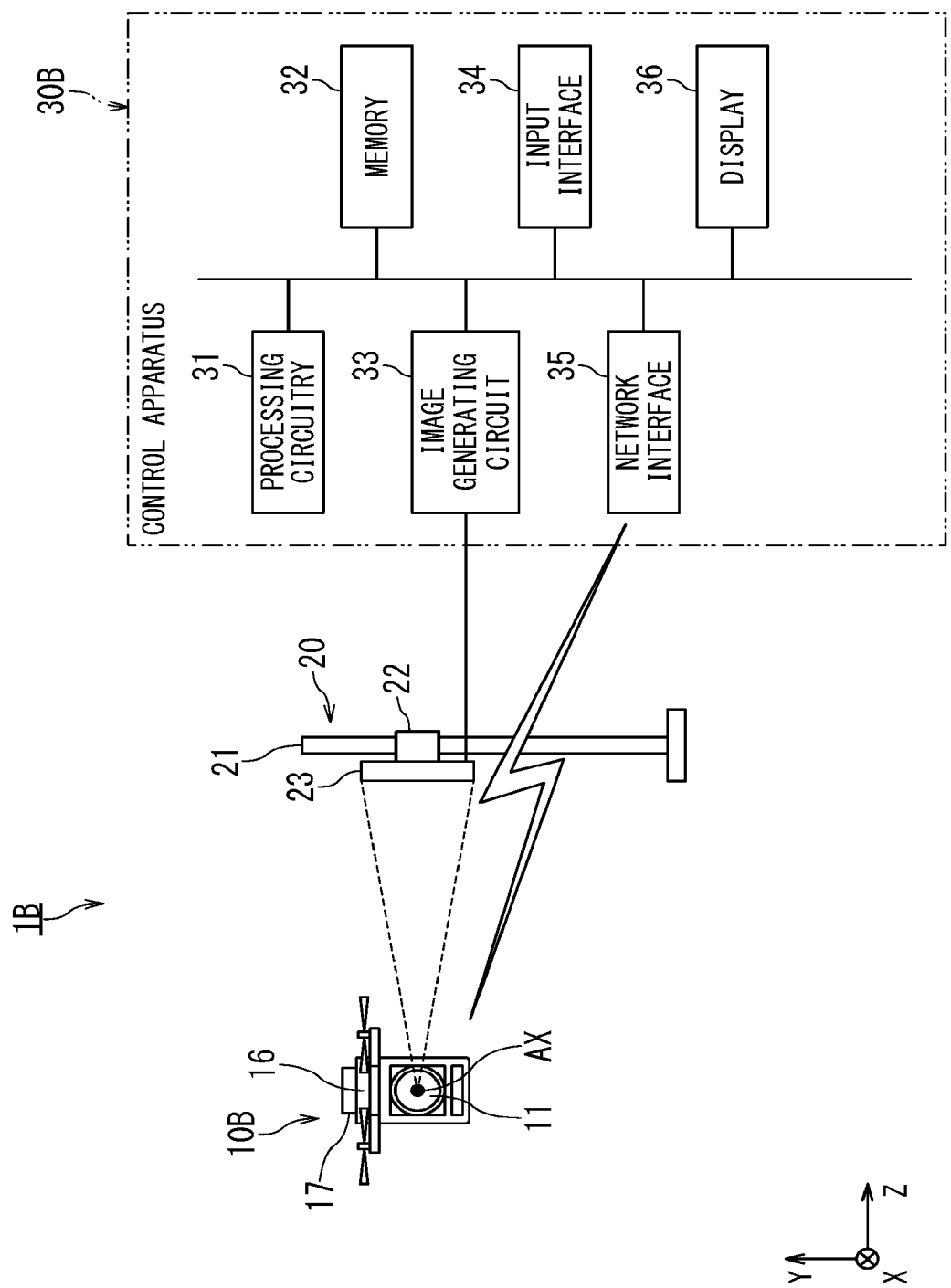
FIG. 11 is a schematic view showing a configuration of an X-ray imaging system including the X-ray tube holding apparatus according to the sixth modified example.

FIG. 11 is a schematic view showing a configuration of an X-ray imaging system including the X-ray tube holding apparatus 10B.

FIG. 11 shows an X-ray imaging system 1B. The X-ray imaging system 1B includes an X-ray tube holding apparatus 10B shown in FIG. 10, a standing posture imaging stand 20, and a control apparatus 30B.

The U-axis of the X-ray tube 11 (shown in FIG. 1) of the X-ray tube holding apparatus 10B, which is parallel to the body axis AX, is parallel to the horizontal axis of the standing detector 23, that is the X-axis, which will be described later. It is assumed that the V-axis of the X-ray tube 11 always coincides with the vertical axis (vertical direction) of the standing detector 23, that is the Y-axis.

The X-ray tube 11 receives power from the high-voltage power supply circuit 16 and emits X-rays to the patient positioned in front of the standing posture imaging stand 20. A movable aperture assembly (not shown) is provided in the front portion of the X-ray tube 11. The movable aperture assembly is an X-ray emission port of the X-ray tube 11, and has slidable blades made of a materials that shields X-rays. Under the control of the processing circuitry 31, the movable aperture assembly can change the X-ray spread angle by opening and closing the X-ray irradiation port. A radiation quality adjusting filter (not shown) may be provided on the front surface of the X-ray tube 11 to adjust the quality of the X-rays generated by the X-ray tube 11.

By controlling the flight of the flying object 13 by the position controlling function 312 of the control apparatus 30B, the X-ray tube 11 of the X-ray tube holding apparatus 10B can be moved to a predetermined position. For example, the X-ray tube 11 can be moved to predetermined three-dimensional coordinates [X, Y, Z].

The control apparatus 30B includes a function of controlling the position and azimuth angle of the X-ray tube 11 by controlling the flight of the flying object 13 of the X-ray tube holding apparatus 10B, a function of controlling the elevation/depression angle of the X-ray tube 11 by controlling the operation of the angle changing member 122 of the X-ray tube holding apparatus 10B, and a function of controlling X-ray imaging. The control apparatus 30B includes a processing circuitry 31, a memory 32, an image generating circuit 33, an input interface 34, a network interface 35, and a display 36. That is, unlike the control apparatus 30 (shown in FIG. 3), the control apparatus 30B does not include the high-voltage power supply circuit 37.

In the X-ray imaging system 1B shown in FIG. 11, the same members as those of the X-ray imaging system 1 shown in FIG. 3 are designated by the same reference numerals, and the description thereof will be omitted. Further, since the functions of the X-ray imaging system 1B are the same as the functions of the X-ray imaging system 1 shown in FIG. 4 except for the functions of the X-ray imaging controlling function 314, the description thereof will be omitted. The X-ray imaging controlling function 314 in the X-ray imaging system 1B has a function of wirelessly controlling the operation of the X-ray tube 11 and the standing posture detector 23 while the X-ray tube holding apparatus 10B is hovering, and wirelessly controlling the power supply from the high-voltage power supply circuit 16 to the X-ray tube 11, thereby controlling X-ray imaging of a patient's examination region located in front of the standing posture detector 23 (or on the lying posture detector 43). Further, since the control method of X-ray imaging by the X-ray imaging system 1B is the same as the control method of X-ray imaging by the X-ray imaging system 1 shown in FIG. 5, the description thereof will be omitted.

As described above, according to the X-ray tube holding apparatus 10B shown in FIG. 11, similar to the X-ray tube holding apparatus 10 (shown in FIG. 1), the movable range of the X-ray tube 11 is not limited by ceiling rails or an arm that holds the X-ray tube 11. Therefore, it is possible to provide the X-ray tube 11 having a high degree of arrangement freedom. Further, if the X-ray tube holding apparatus 10B is applied to the X-ray imaging system 1B, it is possible to perform the X-ray imaging with a large SID. Further, according to the X-ray tube holding apparatus 10B shown in FIG. 11, the movable range of the X-ray tube 11 is not limited since a cable connecting the high-voltage power supply circuit 16 with the commercial power supply is not required. Therefore, it is possible to realize an arrangement with a higher degree of freedom of the X-ray tube 11 compared with the case using the X-ray tube holding apparatus 10 (shown in FIG. 1).

(Method of Using X-ray Tube Holding Apparatuses 10 and 10B, and X-ray Imaging Systems 1 to 1B)

In the above description, using the X-ray tube holding apparatuses 10 and 10B, as well as the X-ray imaging systems 1 to 1B indoors have been described, but it is not limited to that case. For example, the X-ray tube holding apparatuses 10 and 10B, and the X-ray imaging systems 1 to 1B can also be used outdoors (e.g., a disaster area, a battlefield, etc.). Hereinafter, a case where the X-ray tube holding apparatus 10 and the X-ray imaging systems 1 and 1A being used outdoors will be described.

When the X-ray tube holding apparatus 10 and the X-ray imaging system 1A (shown in FIG. 6) are used outdoors, the X-ray imaging system 1A is transported by vehicle to an outdoor destination. When the vehicle arrives at the destination, the X-ray detector is carried out from the vehicle by the operator to be placed on the ground near the examination region of the patient in the lying posture. Further, the position controlling function 312 of the processing circuitry 31 in the vehicle controls the flight of the flying object 13 of the X-ray tube holding apparatus 10 to send the X-ray tube holding apparatus 10 out of the vehicle. The position controlling function 312 sets the position and azimuth angle of the X-ray tube 11. Further, the angle controlling function 313 controls the rotation of the X-ray tube 11 of the X-ray tube holding apparatus 10 while the X-ray tube holding apparatus 10 is hovering. The angle controlling function 313 sets the elevation/depression angle of the X-ray tube 11. The X-ray detector includes multiple position sensors (similar to the position sensors 14 and 15). The position and orientation of the X-ray detector are detected based on the position data of each position sensor of the X-ray detector. The position, azimuth angle, and elevation/depression angle of the X-ray tube 11 are controlled according to the position and orientation of the X-ray detector.

Then, the X-ray imaging controlling function 314 performs X-ray imaging while the X-ray tube holding apparatus 10 is hovering. In this case, for example, the operation of the X-ray imaging system 1A using the lying posture detector 43 shown in FIG. 6 is applied.

On the other hand, when the X-ray tube holding apparatus 10 and the X-ray imaging system 1 (shown in FIG. 3) are used outdoors, the X-ray imaging system 1 is transported by a vehicle to an outdoor destination. When the vehicle arrives at the destination, the X-ray detector is carried out from the vehicle by the operator to be placed on a side of the examination region of the standing or sitting patient. Further, the position controlling function 312 of the processing circuitry 31 in the vehicle controls the flight of the flying object 13 of the X-ray tube holding apparatus 10 to send the X-ray tube holding apparatus 10 out of the vehicle. The position controlling function 312 sets the position and azimuth angle of the X-ray tube 11. Further, the angle controlling function 313 controls the rotation of the X-ray tube 11 of the X-ray tube holding apparatus 10 while the X-ray tube holding apparatus 10 is hovering. the angle controlling function 313 sets the elevation/depression angle of the X-ray tube 11.

Then, the X-ray imaging controlling function 314 performs X-ray imaging while the X-ray tube holding apparatus 10 is hovering. In this case, for example, the operation of the X-ray imaging system 1 using the standing posture detector 23 shown in FIG. 3 is applied.

Note that depending on the outdoor location and the patient's body position, the X-ray detector may not be arranged vertically (standing position detector 23 shown in FIG. 3) or horizontally (lying posture detector 43 shown in FIG. 6). Even in that case, the position, azimuth angle, and elevation/depression angle of the X-ray tube 11 can be controlled according to the position and orientation of the X-ray detector. As a result, X-ray imaging with an appropriate SID is possible.

As described above, the X-ray tube holding apparatuses 10 and 10B and the X-ray imaging systems 1 to 1B can also be used outdoors. Further, when the X-ray tube holding apparatuses 10 and 10B and the X-ray imaging systems 1 to 1B are used outdoors, the operator can perform X-ray imaging by carrying out and arranging only the X-ray detector. Therefore, it is possible to reduce the burden of the operator. Further, when the X-ray tube holding apparatuses 10 and 10B and the X-ray imaging systems 1 to 1B are used outdoors, the position of the X-ray tube holding apparatus 10, the azimuth angle, and elevation/depression angle of the X-ray tube holding apparatus 10 are determined according to the position and orientation of the X-ray detector. Therefore, X-ray imaging with an appropriate SID is available.

According to at least one embodiment described above, it is possible to realize a highly flexible arrangement of an X-ray tube.

While certain embodiments have been described, these embodiments have been presented by way of example only, and are not intended to limit the scope of the inventions. Indeed, the novel methods and systems described herein may be embodied in a variety of other forms; furthermore, various omissions, substitutions, changes, and combinations of embodiments in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray imaging system comprising:
an X-ray tube configured to emit X-rays;
a holding assembly configured to hold the X-ray tube;
a flying object equipped with the holding assembly;
an X-ray detector configured to detect the X-rays emitted by the X-ray tube;
a lying posture imaging table equipped with the X-ray detector, the lying posture imaging table including a table-top and a bed, the table-top being arranged at an upper side of the lying posture imaging table such that a patient can be placed on it, the bed supporting the table-top upward;
a landing assembly attached to the lying posture imaging table such that the table-top is placed between a landing position of the landing assembly and the X-ray detector, the landing assembly being capable of landing the flying object, the landing assembly being equipped with a movable aperture assembly having slidable blades made of materials that shields the X-rays from the X-ray tube; and
processing circuitry configured to control a flight of the flying object, wherein
the processing circuitry is configured to control the flight of the flying object such that the X-ray tube is arranged on a predetermined position with respect to the X-ray detector.

2. The X-ray imaging system according to claim 1, wherein
the holding assembly is configured to further hold an angle changing member changing an emission angle of the X-ray tube;
the processing circuitry is configured to control an operation of the angle changing member such that the X-ray tube faces the X-ray detector.

3. The X-ray imaging system according to claim 2, wherein the processing circuitry is configured to
acquire position data of the X-ray detector, and
control the flight of the flying object based on the position data.

4. The X-ray imaging system according to claim 1, wherein
the processing circuitry is configured to change, when an obstacle is present on a flight route of the flying object, the flight route so as to avoid the obstacle.

5. The X-ray imaging system according to claim 1, wherein
multiple X-ray tube holding apparatuses each including the X-ray tube, the holding assembly and the flying object are provided, and
the processing circuitry is configured to
acquire X-ray image data by controlling an operation of an active X-ray tube holding apparatus among the multiple X-ray tube holding apparatuses, or
acquire X-ray image data for stereoscopic vision by alternately emitting X-rays from two X-ray tubes corresponding to respective two X-ray tube holding apparatuses by controlling an operation of the two X-ray tube holding apparatuses.

6. The X-ray imaging system according to claim 1, wherein
the holding assembly is configured to further hold a high-voltage power supply circuit and a storage battery, and
the processing circuitry is configured to control the high-voltage power supply circuit and the storage battery to control an X-ray imaging.

7. The X-ray imaging system according to claim 1, further comprising an additional cable support apparatus, wherein the cable support apparatus including
a second flying object, and
a support assembly provided below the second flying object and configured to support a cable for supplying power from a high-voltage power supply circuit to the X-ray tube.

8. The X-ray imaging system according to claim 1, wherein
the flying object includes an arm supporting a cable for supplying power from a high-voltage power supply circuit to the X-ray tube.

9. The X-ray imaging system according to claim 1, wherein
the processing circuitry is configured to control an emission of X-rays from the X-ray tube according to flight state of the flying object.

10. The X-ray imaging system according to claim 1, wherein
the bed slides the table-top in the vertical direction, the horizontal direction, and the front-rear direction under the control of the processing circuitry.

11. An X-ray imaging system comprising:
an X-ray tube configured to emit X-rays;
a holding assembly configured to hold the X-ray tube;
a flying object equipped with the holding assembly;
an X-ray detector configured to detect the X-rays emitted by the X-ray tube;
a lying posture imaging table equipped with the X-ray detector, the lying posture imaging table including a table-top and a bed, the table-top being arranged at an upper side of the lying posture imaging table such that a patient can be placed on it, the bed supporting the table-top upward;
a landing assembly attached to the lying posture imaging table such that the table-top is placed between a landing position of the landing assembly and the X-ray detector, the landing assembly being capable of landing the flying object, the landing assembly being equipped with a movable aperture assembly having slidable blades made of materials that shields the X-rays from the X-ray tube; and
processing circuitry configured to control a flight of the flying object, wherein
the processing circuitry is configured to control an emission of X-rays by the X-ray tube according to flight state of the flying object.

12. The X-ray imaging system according to claim 11, wherein
the holding assembly is configured to further hold an angle changing member changing an emission angle of the X-ray tube;
the processing circuitry is configured to control an operation of the angle changing member such that the X-ray tube faces the X-ray detector.

13. The X-ray imaging system according to claim 12, wherein the processing circuitry is configured to
acquire position data of the X-ray detector, and
control the flight of the flying object based on the position data.

14. The X-ray imaging system according to claim 11, wherein
the processing circuitry is configured to change, when an obstacle is present on a flight route of the flying object, the flight route so as to avoid the obstacle.

15. The X-ray imaging system according to claim 11, wherein
multiple X-ray tube holding apparatuses each including the X-ray tube, the holding assembly and the flying object are provided, and
the processing circuitry is configured to
acquire X-ray image data by controlling an operation of an active X-ray tube holding apparatus among the multiple X-ray tube holding apparatuses, or
acquire X-ray image data for stereoscopic vision by alternately emitting X-rays from two X-ray tubes corresponding to respective two X-ray tube holding apparatuses by controlling an operation of the two X-ray tube holding apparatuses.

16. The X-ray imaging system according to claim 11, wherein
the holding assembly is configured to further hold a high-voltage power supply circuit and a storage battery, and
the processing circuitry is configured to control the high-voltage power supply circuit and the storage battery to control an X-ray imaging.

17. The X-ray imaging system according to claim 11, further comprising an additional cable support apparatus, wherein
the cable support apparatus including
a second flying object, and
a support assembly provided below the second flying object and configured to support a cable for supplying power from a high-voltage power supply circuit to the X-ray tube.

18. The X-ray imaging system according to claim 11, wherein
the flying object includes an arm supporting a cable for supplying power from a high-voltage power supply circuit to the X-ray tube.

19. The X-ray imaging system according to claim 11, wherein
the bed slides the table-top in the vertical direction, the horizontal direction, and the front-rear direction under the control of the processing circuitry.

* * * * *